United States Patent
Braun et al.

[11] Patent Number: 6,042,620
[45] Date of Patent: Mar. 28, 2000

[54] P-DIAMINOBENZENE DERIVATIVE COMPOUNDS AND DYE COMPOSITIONS CONTAINING SAME

[75] Inventors: Hans-Juergen Braun, Ueberstorf; Laurent Chassot, Praroman, both of Switzerland

[73] Assignee: Wella AG, Darmstadt, Germany

[21] Appl. No.: 09/257,713

[22] Filed: Feb. 25, 1999

[30] Foreign Application Priority Data

Mar. 19, 1998 [DE] Germany ............ 198 12 059

[51] Int. Cl.[7] .......... A61K 7/13; C07D 207/30; C07D 307/34; C07D 333/04
[52] U.S. Cl. .......... 8/410; 8/407; 8/408; 8/409; 8/411; 8/412; 8/423; 8/574; 8/575; 8/577; 540/1; 548/561; 548/577; 549/74; 549/80; 549/491; 549/505
[58] Field of Search .............. 8/407, 408, 409, 8/410, 411, 412, 423, 574, 575, 577; 540/1; 548/561, 577; 549/74, 80, 491, 505

[56] References Cited

U.S. PATENT DOCUMENTS 4,149,848  4/1979  Bugaut et al. .............. 8/410
5,019,130  5/1991  Flood .......................... 8/423

*Primary Examiner*—Caroline D. Liott
*Attorney, Agent, or Firm*—Michael J. Striker

[57] ABSTRACT

New p-diaminobenzene derivative compounds of the formula (I):

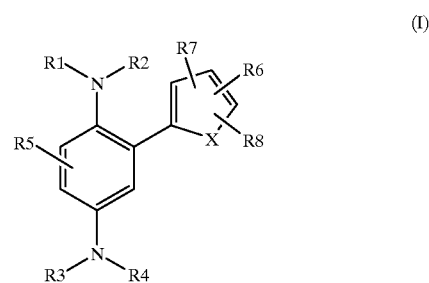

(I)

and physiologically compatible water soluble salts thereof are described, wherein X represents oxygen, sulfur, selenium or N-R9, wherein R9 represents hydrogen, an alkyl group, a hydroxyalkyl group, a phenyl group or an acetyl group; and the remaining R groups each represent variously hydrogen, hydroxy, amino, nitro, nitrile, alkyl, alkoxy, hydroxyalkyl, cyclic or aromatic groups, among others. Compositions for dyeing keratin fibers including a combination of coupler and developer substance are disclosed, in which the developer substance includes at least one of the new p-diaminobenzene derivative compounds.

19 Claims, No Drawings

P-DIAMINOBENZENE DERIVATIVE COMPOUNDS AND DYE COMPOSITIONS CONTAINING SAME

The present invention relates to new p-diaminobenzene derivative compounds and compositions for dyeing keratin fibers containing these new compounds.

Oxidation dye compounds have long attained substantial importance in the art of dyeing keratin fibers, especially hair dyeing. The dyeing caused by those compounds occurs by reaction of certain developer substances with certain coupler substances in the presence of a suitable oxidizing agent. For example, 2,5-diaminotoluene, 2,5-diaminophenylethylalcohol, p-aminophenol and 1,4-diaminobenzene can be mentioned as developer substances, while resorcinol, 4-chlororesorcinol, 1-naphthol, 3-aminophenol and derivatives of m-phenylendiamine can be mentioned as coupler substances.

There are numerous additional requirements for oxidation dye compounds that are used to dye human hair besides the color or the desired intensity. Thus the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore an additional requirement is the production of a broad palette of different color shades using different developer and coupler substances.

It is not possible to fulfill all the above-mentioned requirements with the currently known dye compounds.

SUMMARY OF THE INVENTION

It is an object of the present invention to provide improved developer compounds that fulfill the above-described requirements in a special manner.

It has now been surprisingly found that the new p-diaminobenzene derivative compounds according to formula (I) fulfill the requirements for developer compounds to an especially great extent. Particularly bright or intense color shades are produced using these developer substances with most known coupler substances, which are however extraordinarily light fast and fast to washing.

The subject matter of the present invention thus includes a composition for oxidative dyeing of keratin fibers, for example, hair, fur, feathers or wool, especially human hair, based on a developer substance-coupler substance combination, which includes at least one diaminobenzene derivative compound of the following formula (I):

$$\text{(I)}$$

wherein X represents oxygen, sulfur, selenium or N-R9;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the R1 to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 and R8 each represents, independently of each other, hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 represents hydrogen, a halogen atom, a $C_1$- to $C_6$-alkyl group or a —C(O)H group;

R9 represents hydrogen, a $C_1$- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11, R13 and R16 each, independently of each other, represents hydrogen or a $C_1$- to $C_4$-alkyl group;

R12 represents an amino group or a nitrile group;

R14, R17 and R18 each, independently of each other, represents hydrogen, a hydroxy group, a $C_1$- to $C_4$-alkyl group a $C_1$- to $C_4$-hydroxyalkyl group, a $C_3$- to $C_4$-dihydroxyalkyl group or a group of formula (II):

$$\text{(II)}$$

and R15 represents hydrogen, an amino group or a hydroxy group;

or its physiologically compatible water-soluble salt.

The compounds of formula (I) can be, for example: 2,5-diamino-(2-thienyl)benzene; 2-amino-5-methylamino-(2-thienyl)benzene; 5-amino-2-methylamino-(2-thienyl)benzene; 2-amino-5-dimethylamino-(2-thienyl)benzene; 5-amino-2-dimethylamino-(2-thienyl)benzene; 2-amino-5-(2-hydroxyethyl)amino-(2-thienyl)benzene; 5-amino-2-(2-hydroxyethyl)amino-(2-thienyl)benzene; 2-amino-5-di(2-hydroxyethyl)amino-(2-thienyl)benzene; 5-amino-2-di(2-hydroxyethyl)amino-(2-thienyl)benzene; 2-amino-5-(2-hydroxyethyl)-methylamino-(2-thienyl)benzene; 5-amino-2-(2-hydroxyethyl)-methylamino-(2-thienyl)benzene; 2-amino-5-(2,3-dihydroxypropyl)amino-(2-thienyl)benzene; 5-amino-2-(2,3-dihydroxypropyl)amino-(2-thienyl)benzene; 2-amino-5-di(2,3-dihydroxypropyl)amino-(2-thienyl)benzene; 5-amino-2-di(2,3-dihydroxypropyl)amino-(2-thienyl)benzene; 2-amino-5-(2,3-dihydroxypropyl)methylamino-(2-thienyl)benzene; 5-amino-2-(2,3-dihydroxypropyl)methylamino(2-thienyl)benzene; 2-amino-5-(2-methoxyethyl)amino-(2-thienyl)benzene; 5-amino-2-(2-methoxy-ethyl)amino-(2-thienyl)benzene; 2-amino-5-di(2-methoxyethyl)amino-(2-thienyl)benzene; 5-amino-2-di(2-methoxyethyl)amino-(2-thienyl)benzene; 2-amino-5-(2-methoxyethyl)methylamino-(2-thienyl)benzene; 5-amino-2-(2-methoxyethyl)methylamino- (2-thienyl)benzene; 2-amino-5-methylamino-(2-furyl) benzene; 5-amino-2-methylamino-(2-furyl)benzene; 2-amino-5-dimethylamino-(2-furyl)benzene; 5-amino-2-dimethylamino-(2-furyl)benzene; 2-amino-5-(2-hydroxyethyl)amino-(2-furyl)benzene; 5-amino-2-(2-hydroxyethyl)amino-(2-furyl)benzene; 2-amino-5-di(2-hydroxyethyl)amino-(2-furyl)benzene; 5-amino-2-di(2-hydroxyethyl)-amino-(2-furyl)benzene; 2-amino-5-(2-hydroxyethyl)methylamino-(2-furyl)benzene; 5-amino-2-(2-hydroxyethyl)methylamino-(2-furyl)benzene; 2-amino-5-(2,3-dihydroxypropyl)amino-(2-furyl)-benzene; 5-amino-2-(2,3-dihydroxypropyl)amino-(2-furyl)-benzene; 2-amino-5-di(2,3-dihydroxypropyl)amino-(2-furyl)-benzene; 5-amino-2-di(2,3-dihydroxypropyl)amino-(2-furyl)-benzene; 2-amino-5-(2,3-dihydroxypropyl)methylamino-(2-furyl)benzene; 5-amino-2-(2,3-dihydroxypropyl)methylamino-(2-furyl)benzene; 2-amino-5-(2-methoxyethyl)amino-(2-furyl)benzene; 5-amino-2-(2-methoxyethyl)amino-(2-furyl)-benzene; 2-amino-5-di(2-methoxyethyl)amino-(2-furyl)benzene; 5-amino-2-di(2-methoxyethyl)amino-(2-furyl)benzene; 2-amino-5-(2-methoxyethyl)methylamino-(2-furyl)benzene; 5-amino-2-(2-methoxyethyl)methylamino-(2-furyl)benzene; 2-amino-5-methylamino(pyrrol-2-yl)benzene; 5-amino-2-methylamino-(pyrrol-2-yl)benzene; 2-amino-5-dimethylamino-(pyrrol-2-yl)benzene; 5-amino-2-dimethylamino-(pyrrol-2-yl)benzene; 2-amino-5-(2-hydroxyethyl)amino-(pyrrol-2-yl)benzene; 5-amino-2-(2-hydroxyethyl)amino-(pyrrol-2-yl)benzene; 2-amino-5-di(2-hydroxyethyl)amino-(pyrrol-2-yl)benzene; 5-amino-2-di(2-hydroxy-ethyl)amino-(pyrrol-2-yl)benzene; 2-amino-5-(2-hydroxyethyl)-methylamino-(pyrrol-2-yl)benzene; 5-amino-2-(2-hydroxyethyl)-methylamino-(pyrrol-2-yl) benzene; 2-amino-5(2,3-dihydroxypropyl)amino-(pyrrol-2-yl)benzene; 5-amino-2-(2,3-dihydroxypropyl)amino-(pyrrol-2-yl)benzene; 2-amino-5-di(2,3-dihydroxypropyl)-amino-(pyrrol-2-yl)benzene; 5-amino-2-di(2,3-dihydroxypropyl)amino-(pyrrol-2-yl)benzene; 2-amino-5-(2,3-dihydroxypropyl)methylamino-(pyrrol- 2-yl)benzene; 5-amino-2-(2,3-dihydroxypropyl)methylamino-(pyrrol-2-yl)benzene; 2-amino-5-(2-methoxyethyl)amino-(pyrrol-2-yl)benzene; 5-amino-2-(2-methoxyethyl)amino(pyrrol-2-yl)benzene; 2-amino-5-di(2-methoxyethyl)amino-(pyrrol-2-yl)benzene; 5-amino-2-di(2-methoxyethyl)amino(pyrrol-2-yl)benzene; 2-amino-5-(2-methoxyethyl)-methylamino(pyrrol-2-yl)benzene; 5-amino-2-(2-methoxyethyl)methylamino-(pyrrol-2-yl)benzene; 2-amino-5-methylamino-(1-methyl-1H-pyrrol-2-yl)benzene; 5-amino-2-methylamino-(1-methyl-1H-pyrrol-2-yl)benzene; 2-amino-5-dimethylamino-(1-methyl-1H-pyrrol-2-yl)benzene; 5-amino-2-dimethylamino(1-methyl-1H-pyrrol-2-yl) benzene; 2-amino-5-(2-hydroxyethyl)amino-(1-methyl-1H-pyrrol-2-yl)benzene; 5-amino-2-(2-hydroxyethyl) amino-(1-methyl-1H-pyrrol-2-yl)benzene; 2-amino-5-di(2-hydroxyethyl)amino-(1-methyl-1H -pyrrol-2-yl)benzene; 5-amino-2-di(2-hydroxyethyl)amino-(1-methyl-1H-pyrrol-2-yl)-benzene; 2-amino-5-(2-hydroxyethyl)-methylamino-(1-methyl-1H-pyrrol-2-yl)benzene; 5-amino-2-(2-hydroxyethyl)methylamino-(1-methyl-1H-pyrrol-2-yl) benzene; 2-amino-5-(2,3-dihydroxypropyl)amino-(1-methyl-1H-pyrrol-2-yl)benzene; 5-amino-2-(2,3-dihydroxypropyl)amino-(1-methyl-1H-pyrrol-2-yl)benzene; 2-amino-5-di(2,3-dihydroxypropyl)-amino-(1-methyl-1H-pyrrol-2-yl)benzene; 5-amino-2-di(2,3-dihydroxypropyl) amino-(1-methyl-1H-pyrrol-2-yl)benzene; 2-amino-5-(2,3-dihydroxypropyl)-methylamino-(1-methyl-1H-pyrrol-2-yl) benzene; 5-amino-2-(2,3-dihydroxypropyl)methylamino-(1-methyl-1H-pyrrol-2-yl)benzene; 2-amino-5-(2-methoxyethyl)amino-(1-methyl-1H-pyrrol-2-yl)benzene; 5-amino-2-(2-methoxyethyl)amino-(1-methyl-1H-pyrrol-2-yl)benzene; 2-amino-5-di(2-methoxyethyl)amino-(1-methyl-1H-pyrrol-2-yl)benzene; 5-amino-2-di(2-methoxyethyl)-amino-(1-methyl-1H-pyrrol-2-yl)benzene; 2-amino-5-(2-methoxyethyl)methylamino-(1-methyl-1H-pyrrol-2-yl)benzene; 5-amino-2-(2-methoxyethyl) methylamino-(1-methyl-1H-pyrrol-2-yl)benzene; 2,5-diamino-3-methyl-(2-thienyl)benzene; 2-amino-5-di(2-hydroxyethyl)amino-3-methyl(2-thienyl)benzene; 5-amino-2-di(2-hydroxyethyl)amino-3-methyl-(2-thienyl)benzene; 2,5-diamino-3-chloro-(2-thienyl)benzene; 2-amino-5-di(2-hydroxyethyl)amino-3-chloro-(2-thienyl)benzene; 5-amino-2-di(2-hydroxyethyl)-amino-3-chloro-(2-thienyl)benzene; 2,5-diamino-4-methyl-(2-thienyl)benzene; 2-amino-5-di(2-hydroxyethyl)amino-4-methyl-(2-thienyl)benzene; 5-amino-2-di(2-hydroxyethyl)amino-4-methyl-(2-thienyl) benzene; 2,5-diamino-4-chloro-(2-thienyl)benzene; 2-amino-5-di(2-hydroxyethyl)amino-4-chloro-(2-thienyl) benzene; 5-amino-2-di(2-hydroxyethyl)amino-4-chloro-(2-thienyl)benzene; 2,5-diamino-5-methyl-(2-thienyl)-benzene; 2-amino-5-di(2-hydroxyethyl)amino-5-methyl-(2-thienyl)benzene; 5-amino-2-di(2-hydroxyethyl)amino-5-methyl-(2-thienyl)benzene; 2,5-diamino-5-chloro-(2-thienyl)benzene; 2-amino-5-di(2-hydroxyethyl)amino-5-chloro-(2-thienyl)benzene; 5-amino-2-di(2-hydroxyethyl) amino-5-chloro-(2-thienyl)benzene; 2,5-diamino-3-methyl-(2-furyl)benzene; 2-amino-5-di-(2-hydroxy-ethyl)amino-3-methyl-(2-furyl)-benzene; 5-amino-2-di(2-hydroxyethyl) amino-3-methyl-(2-furyl)benzene; 2,5-diamino- 3-chloro-(2-furyl)benzene; 2-amino-5-di(2-hydroxyethyl)-amino-3-chloro-(2-furyl)benzene; 5-amino-2-di(2-hydroxyethyl) amino-3-chloro-(2-furyl)benzene; 2,5-diamino-4-methyl-(2-furyl)-benzene; 2-amino-5-di(2-hydroxyethyl)amino-4-methyl-(2-furyl)benzene; 5-amino-2-di(2-hydroxyethyl) amino-4-methyl-(2-furyl)benzene; 2,5-diamino-4-chloro-(2-furyl)benzene; 2-amino-5-di(2-hydroxy-ethyl)amino-4-chloro-(2-furyl)benzene; 5-amino-2-di(2-hydroxyethyl) amino-4-chloro-(2-furyl)benzene; 2,5-diamino-5-methyl-(2-furyl)benzene; 2-amino-5-di(2-hydroxyethyl)-amino-5-methyl-(2-furyl)benzene; 5-amino-2-di(2-hydroxyethyl)-amino-5-methyl-(2-furyl)benzene; 2,5-diamino-5-chloro-(2-furyl)benzene; 2-amino-5-di(2-hydroxyethyl)amino-5-chloro-(2-furyl)benzene; 5-amino-2-di(2-hydroxyethyl)-amino-5-chloro-(2-furyl)benzene; 2,5-diamino-3-methyl-(pyrrol-2-yl)-benzene; 2-amino-5-di(2-hydroxyethyl) amino-3-methyl-(pyrrol-2-yl)benzene; 5-amino-2-di(2-hydroxyethyl)amino-3-methyl-(pyrrol-2-yl)benzene; 2,5-diamino-3-chloro-(pyrrol-2-yl)-benzene; 2-amino-5-di(2-hydroxyethyl)-amino-3-chloro-(pyrrol-(2-yl) benzene; 5-amino-2-di(2-hydroxyethyl)amino-3-chloro-(pyrrol-2-yl) benzene; 2,5-diamino-4-methyl-(pyrrol-2-yl)-benzene; 2-amino-5-di(2-hydroxyethyl)amino-4-methyl-(pyrrol-2-yl) benzene; 5-amino-2-di(2-hydroxyethyl)amino-4-methyl-(pyrrol-2-yl)benzene; 2,5-diamino-4-chloro-(pyrrol-2-yl)-benzene; 2-amino-5-di(2-hydroxyethyl)-amino-4-chloro (pyrrol-2-yl)benzene; 5-amino-2-di(2-hydroxyethyl)amino-4-chloro-(pyrrol-2-yl)benzene; 2,5-diamino-5-methyl-(pyrrol-2-yl)-benzene; 2-amino-5-di(2-hydroxyethyl) amino-5-methyl-(pyrrol-2-yl)benzene; 5-amino-2-di(2-hydroxyethyl)amino-5-methyl-(pyrrol-2-yl)benzene; 2,5-diamino-5-chloro-(pyrrol-2-yl)-benzene; 2-amino-5-di(2-hydroxyethyl)amino-5-chloro-(pyrrol-2-yl)benzene; 5-amino-2-di(2-hydroxyethyl)amino-5-chloro-(pyrrol-2-yl) benzene; 2,5-diamino-3-methyl-(1-methyl-1H-pyrrol-2-yl) benzene; 2-amino-5-di(2-hydroxyethyl)amino-3-methyl-(1- methyl-1H-pyrrol-2-yl)benzene; 5-amino-2-di(2-hydroxyethyl)amino-3-methyl-(1-methyl-1H-pyrrol-2-yl)benzene; 2,5-diamino-3-chloro-(1-methyl-1H-pyrrol-2-yl)benzene; 2-amino-5-di(2-hydroxyethyl)amino-3-chloro-(1-methyl-1H-pyrrol-2-yl)benzene; 5-amino-2-di(2-hydroxyethyl)amino-3-chloro-(1-methyl-1H-pyrrol-2-yl)benzene; 2,5-diamino-4-methyl-(1-methyl-1H-pyrrol-2-yl)benzene; 2-amino-5-di(2-hydroxyethyl)-amino-4-methyl-(1-methyl-1H-pyrrol-2-yl)benzene; 5-amino-2-di(2-hydroxyethyl)amino-4-methyl-(1-methyl-1H-pyrrol-2-yl)-benzene; 2,5-diamino-4-chloro-(1-methyl-1H-pyrrol-2-yl)-benzene; 2-amino-5-{di(2-hydroxyethyl)amino}-4-chloro-(1-methyl-1H-pyrrol-2-yl)benzene; 5-amino-2-di(2-hydroxyethyl)-amino-4-chloro-(1-methyl-1H- pyrrol-2-yl)benzene; 2,5-diamino-5-methyl-(1-methyl-1H-pyrrol-2-yl)benzene; 2-amino-5-di(2-hydroxyethyl)amino-5-methyl-(1-methyl-1H-pyrrol-2-yl)benzene; 5-amino-2-di(2-hydroxyethyl)amino-5-methyl-(1-methyl-1H-pyrrol-2-yl)benzene; 2,5-diamino-5-chloro-(1-methyl-1H-pyrrol-2-yl)benzene; 2-amino-5-di(2-hydroxyethyl)amino-5-chloro-(1-methyl-1H-pyrrol-2-yl)benzene; 5-amino-2-di(2-hydroxyethyl)amino-5-chloro-(1-methyl-1H-pyrrol-2-yl)benzene; 2,5-diamino-(3-methyl-2-thienyl)benzene; 2-amino-5-di(2-hydroxyethyl)amino-(3-methyl-2-thienyl)benzene; 5-amino-2-di(2-hydroxyethyl)amino-(3-methyl-2-thienyl)benzene; 2,5-diamino-(3-methyl-2-furyl)benzene; 2-amino-5-di(2-hydroxyethyl)amino-(3-methyl-2-furyl)benzene; 5-amino-2-di(2-hydroxyethyl)amino-(3-methyl-2-furyl)benzene; 2,5-diamino-(4-methyl-2-thienyl)benzene; 2-amino-5-di-(2-hydroxyethyl)amino-(4-methyl-2-thienyl)benzene; 5-amino-2-di(2-hydroxyethyl)amino-(4-methyl-2-thienyl)benzene; 2,5-diamino-(4-methyl-2-furyl)benzene; 2-amino-5-di(2-hydroxyethyl)amino-(4-methyl-2-furyl)benzene; 5-amino-2-di(2-hydroxyethyl)amino-(4-methyl-2-furyl)benzene; 2,5-diamino-(5-methyl-2-thienyl)benzene; 2-amino-5-di(2-hydroxyethyl)-amino-(5-methyl-2-thienyl)benzene; 5-amino-2-di(2-hydroxyethyl)amino-(5-methyl-2-thienyl)benzene; 2,5-diamino-(5-methyl-2-furyl)benzene; 2-amino-5-di(2-hydroxyethyl)-amino-(5-methyl-2-furyl)benzene; 5-amino-2-di(2-hydroxyethyl)amino-(5-methyl-2-furyl)benzene; 2,5-diamino-(3-ethyl-2-thienyl)-benzene; 2-amino-5-di(2-hydroxyethyl)amino-(3-ethyl-2-thienyl)benzene; 5-amino-2-di(2-hydroxyethyl)amino-(3-ethyl-2-thienyl)benzene; 2,5-diamino-(3-ethyl-2-furyl)-benzene; 2-amino-5-di(2-hydroxyethyl)amino-(3-ethyl-2-furyl)benzene; 5-amino-2-di(2-hydroxyethyl)amino-(3-ethyl-2-furyl)benzene; 2,5-diamino-(4-ethyl-2-thienyl)benzene; 2-amino-5-di(2-hydroxyethyl)amino-(4-ethyl-2-thienyl)benzene; 5-amino-2-di(2-hydroxyethyl)amino-(4-ethyl-2-thienyl)-benzene; 2,5-diamino-(4-ethyl-2-furyl)benzene; 2-amino-5-di(2-hydroxyethyl)amino-( 4-ethyl-2-furyl)benzene; 5-amino-2-di(2-hydroxyethyl)amino-(4-ethyl-2-furyl)benzene; 2,5-diamino-(5-ethyl-2-thienyl)-benzene; 2-amino-5-di(2-hydroxy-ethyl)amino-(5-ethyl-2-thienyl)benzene; 5-amino-2-di(2-hydroxyethyl)amino-(5-ethyl-2-thienyl)benzene; 2,5-diamino-(5-ethyl-2-furyl)benzene; 2-amino-5-di(2-hydroxyethyl)amino-(5-ethyl-2-furyl)benzene; 5-amino-2-di(2-hydroxyethyl)amino-(5-ethyl-2-furyl)benzene; 2,5-diamino-(3-dimethylamino-2-thienyl)benzene; 2-amino-5-di(2-hydroxyethyl)amino-(3-dimethylamino-2-thienyl)benzene; 5-amino-2-di(2-hydroxy-ethyl)amino-(3-dimethylamino-2-thienyl)benzene; 2,5-diamino-(3-dimethylamino-2-furyl)benzene; 2-amino-5-di(2-hydroxy-ethyl)amino-(3-dimethylamino-2-furyl)benzene; 5-amino-2-di(2-hydroxyethyl)amino-(3-dimethylamino-2-furyl)benzene; 2,5-diamino-(4-dimethylamino-2-thienyl)benzene; 2-amino-5-di(2-hydroxy-ethyl)amino-(4-dimethylamino-2-thienyl)benzene; 5-amino-2-di(2-hydroxy-ethyl)amino-(4-dimethylamino-2-thienyl)benzene; 2,5-diamino-(4-dimethyl-amino-2-furyl)-benzene; 2-amino-5-di(2-hydroxyethyl)amino-(4-dimethyl-amino-2-furyl)benzene; 5-amino-2-di(2-hydroxyethyl)amino-(4-dimethyl-amino-2-furyl)benzene; 2,5-diamino-(5-dimethyl-amino-2-thienyl)benzene; 2-amino-5-di(2-hydroxyethyl)amino-(5-dimethylamino-2-thienyl)benzene; 5-amino-2-di(2-hydroxy-ethyl)amino-(5-dimethylamino-2-thienyl)benzene; 2,5-diamino-(5-dimethylamino-2-furyl)benzene; 2-amino-5-di(2-hydroxy-ethyl)amino-(5-dimethylamino-2-furyl)benzene; 5-amino-2-di(2-hydroxyethyl)amino-(5-dimethylamino-2-furyl)benzene; 2,5-diamino-(3-formyl-2-thienyl)benzene; 2-amino-5-di(2-hydroxyethyl)amino-(3-formyl-2-thienyl)benzene; 5-amino-2-di(2-hydroxyethyl)amino-(3-formyl-2-thienyl)benzene; 2,5-diamino-(3-formyl-2-furyl)-benzene; 2-amino-5-di(2-hydroxyethyl)amino-(3-formyl-2-furyl)benzene; 5-amino-2-di(2-hydroxyethyl)amino-(3-formyl-2-furyl)benzene; 2,5-diamino-(4-formyl-2-thienyl)benzene; 2-amino-5-di(2-hydroxyethyl)amino-(4-formyl-2-thienyl)benzene; 5-amino-2-di(2-hydroxyethyl)amino-(4-formyl-2-thienyl)benzene; 2,5-diamino-(4-formyl-2-furyl)benzene; 2-amino-5-di(2-hydroxy-ethyl)amino-(4-formyl-2-furyl)benzene; 5-amino-2-di(2-hydroxy-ethyl)amino-(4-formyl-2-furyl)benzene; 2,5-diamino-(5-formyl-2-thienyl)benzene; 2-amino-5-di(2-hydroxyethyl)amino-(5-formyl-2-thienyl)benzene; 5-amino-2-di(2-hydroxyethyl)amino-(5-formyl-2-thienyl)benzene; 2,5-diamino-(5-formyl-2-furyl)benzene; 2-amino-5-di(2-hydroxyethyl)amino-(5-formyl-2-furyl)benzene; 5-amino-2-di(2-hydroxyethyl)amino-(5-formyl-2-furyl)benzene; 2,5-diamino-(3-acetyl-2-thienyl)benzene; 2-amino-5-di(2-hydroxy-ethyl)amino-(3-acetyl-2-thienyl)benzene; 5-amino-2-di(2-hydroxyethyl)amino-(3-acetyl-2-thienyl)benzene; 2,5-diamino-(3-acetyl-2-furyl)benzene; 2-amino-5-di(2-hydroxyethyl)-amino-(3-acetyl-2-furyl)benzene; 5-amino-2-di(2-hydroxy-ethyl)amino-(3-acetyl-2-furyl)benzene; 2,5-diamino-(4-acetyl-2-thienyl)benzene; 2-amino-5-di(2-hydroxyethyl)amino-(4-acetyl-2-thienyl)benzene; 5-amino-2-di(2-hydroxyethyl)-amino-(4-acetyl-2-thienyl)benzene; 2,5-diamino-(4-acetyl-2-furyl)benzene; 2-amino-5-di(2-hydroxyethyl)amino-(4-acetyl-2-furyl)benzene; 5-amino-2-di(2-hydroxyethyl)amino-(4-acetyl-2-furyl)benzene; 2,5-diamino(5-acetyl-2-thienyl)-benzene; 2-amino-5-di(2-hydroxyethyl)amino-(5-acetyl-2-thienyl)benzene; 5-amino-2-di(2-hydroxyethyl)amino-(5-acetyl-2-thienyl)benzene;

2,5-diamino-(5-acetyl-2-furyl)-benzene; 2-amino-5-di(2-hydroxyethyl)amino-(5-acetyl-2-furyl)benzene; 5-amino-2-di(2-hydroxyethyl)amino-(5-acetyl-2-furyl)benzene; 2,5-diamino-(3-aminomethyl-2-thienyl)benzene; 2-amino-5-di(2-hydroxyethyl)amino-(3-aminomethyl-2-thienyl)-benzene; 5-amino-2-di(2-hydroxyethyl)amino-(3-aminomethyl-2-thienyl)benzene;2,5-diamino-(3-aminomethyl-2-furyl)benzene; 2-amino-5-di(2-hydroxyethyl)amino-(3-aminomethyl-2-furyl)-benzene; 5-amino-2-di(2-hydroxyethyl)amino-(3-aminomethyl-2-furyl)benzene; 2,5-diamino-(4-aminomethyl-2-thienyl)-benzene; 2-amino-5-di-(2-hydroxyethyl)amino-(4-aminomethyl-2-thienyl)benzene; 5-amino-1) 2-di(2-hydroxyethyl)amino-(4-aminomethyl-2-thienyl)benzene; 2,5-diamino-(4-aminomethyl-2-furyl)benzene; 2-amino-5-di(2-hydroxyethyl)amino-(4-aminomethyl-2-furyl)benzene; 5-amino-2-di(2-hydroxyethyl)-amino-(4-aminomethyl-2-furyl)benzene; 2,5-diamino-(5-aminomethyl-2-thienyl)benzene; 2-amino-5-di(2-hydroxy-ethyl)amino-(5-aminomethyl-2-thienyl)benzene; 5-amino-2-di(2- hydroxyethyl)amino-(5-aminomethyl-2-thienyl)benzene; 2,5-diamino-(5-aminomethyl-2-furyl)benzene; 2-amino-5-di(2-hydroxyethyl)amino-(5-aminomethyl-2-furyl)benzene; 5-amino-2-di(2-hydroxyethyl)amino-(5-aminomethyl-2-furyl)benzene; 2,5-diamino-(3-(2-hydroxyethyl(imino))methylene-2-thienyl)-benzene; 2-amino-5-di(2-hydroxyethyl)amino-(3-(2-hydroxy-ethyl(imino))methylen-2-thienyl)benzene; 5-amino-2-di(2-hydroxyethyl)amino-(3-(2-hydroxyethyl(imino))-methylen-2-thienyl)benzene; 2,5-diamino-(3-(2-hydroxyethyl-(imino))methylen-2-furyl)benzene; 2-amino-5-di(2-hydroxy-ethyl)amino-(3-(2-hydroxyethyl(imino))methylen-2-furyl)-benzene; 5-amino-2-di(2-hydroxyethyl)amino-(3-(2-hydroxy-ethyl(imino))methylen-2-furyl)benzene; 2,5-diamino-(4-(2-hydroxyethyl(imino)) methylen-2-thienyl)benzene; 2-amino-5-di(2-hydroxyethyl)amino-(4-(2-hydroxyethyl(imino))-methylen-2-thienyl)benzene; 5-amino-2-di(2-hydroxy-ethyl)amino-(4-(2-hydroxyethyl-(imino))methylen-2-thienyl)benzene; 2,5-diamino-(4-(2-hydroxyethyl-(imino))-methylen-2-furyl)benzene; 2-amino-5-di(2-hydroxyethyl)-amino-(4-(2-hydroxyethyl(imino))methylen-2-furyl)benzene; 5-amino-2-di(2-hydroxyethyl)amino-(4-(2-hydroxyethyl(imino))methylen-2-furyl)benzene; 2,5-diamino-(5-(2-hydroxy-ethyl(imino)) methylene-2-thienyl)benzene; 2-amino-5-di(2-hydroxyethyl)amino-(5-(2-hydroxyethyl(imino))methylen-2-thienyl) benzene; 5-amino-2-di(2-hydroxyethyl)amino-(5-(2-hydroxyethyl(imino))methylen-2-thienyl)benzene; 2,5-diamino-(5-(2-hydroxyethyl(imino))methylen-2-furyl)benzene; 2-amino-5-di(2-hydroxyethyl)amino-(5-(2-hydroxyethyl-(imino))methylen-2-furyl)benzene and 5-amino-2-di(2-hydroxyethyl)amino-(5-(2-hydroxyethyl(imino))methylen-2-furyl)benzene.

Preferred compounds of formula (I) include those in which (i) one or more of the groups R5, R6, R7 and R8 are hydrogen and/or (ii) R1, R2, R3 and R4 are simultaneously hydrogen and/or (iii) R7 is hydrogen and R6 is hydrogen, —C(O)H, —C(O)CH$_3$, C$_1$–C$_4$-alkyl or C$_1$–C$_4$-hydroxyalkyl (particularly R6=R7=hydrogen).

Particularly the following compounds are named: 2,5-diamino-1-(2-thienyl)benzene; 2,5-diamino-1-(2-furyl)benzene; 2,5-diamino-1-(3-acetyl-2-thienyl)benzene; 2,5-diamino-1-(3-chloro-2-thienyl)benzene; 2,5-diamino-1-(1H-pyrrol-2-yl)benzene; 2,5-diamino-1-(3-methyl-2-thienyl)-benzene; 2,5-diamino-1-(5-methyl-2-thienyl)benzene; 2,5-diamino-1-(3-nitro-2-thienyl)benzene; 2-dimethylamino-5-amino-1-(2-thienyl)benzene; 2-pyrrolidino-5-amino-1-(2-thienyl)-benzene, 2-Di(2-hydroxyethyl)amino-5-amino-1-(2-thienyl)benzene, 2-(2-hydroxyethyl)amino-5-amino -1-(2-thienyl)benzene, 2-(2-methoxyethyl)amino-5-amino-1-(2-thienyl)benzene, 2-(2,3-dihydroxypropyl)amino-5-amino-1-(2-thienyl)benzene, 2,5-diamino-4-methoxy-1-(2-thienyl)benzene, 2,5-diamino-4-methyl-1-(2-thienyl)benzene, 2,5-diamino-1-(3-chloro-2-thienyl)benzene, 2,5-diamino-1-(1-methylpyrrol-2-yl)-benzene and 2,5-diamino-1-(3-formyl-2-thienyl)benzene.

The compounds of formula (I) can be used both as free bases and also in the form of their physiologically compatible salts with inorganic or organic acids, for example hydrochloric acid, sulfuric acid, phosphoric acid, acetic acid, propionic acid, lactic acid or citric acid.

The diaminobenzene derivative compound of formula (I) is contained in the dye composition according to the invention in an amount of from about 0.005 to 20 percent by weight, preferably however from about 0.01 to 5.0 percent by weight, and especially preferably from 0.1 to 2.5 percent by weight.

The coupler substance preferably can be 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-amino-ethyl)amino]aniline, 1,3-di(2,4-diaminophenoxy)propane, di(2,4-diaminophenoxy) methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy- 2-methyphenol, 5-amino-4-ethoxy-2-methylphenol, 3-amino-2,4-dicholorophenol, 5-amino-2,4-dichlorophenol, 3-amino-2-methylphenol, 3-amino-2-chloro-6-methylphenol, 3-aminophenol, 2-[(3-hydroxyphenyl)amino]-acetamide, 5-[(2-hydroxyethyl)amino]-2-methylphenol, 3-[(2-hydroxyethyl)-aminophenol, 3-[(2-methoxyethyl)amino]phenol, 5-amino-2-ethylphenol, 2-(4-amino-2-hydroxyphenoxy)ethanol, 5-[(3-hydroxypropyl) amino]-2-methylphenol, 3-[(2,3-dihydroxypropyl)-amino]-2-methylphenol, 3-[(2-hydroxyethyl)amino]-2-methyl-phenol, 2-amino-3-hydroxypyridine, 5-amino-4-chloro-2-methyl-phenol, 1-naphthol, 1,5-dihydroxynaphthalene, 1,7-dihydroxy-naphthalene, 2,3-dihydrocynaphthalene, 2,7-dihydroxy-naphthalene, 2-methyl-1-naphthol acetate, 1,3-dihydroxy-benzene, 1-chloro-2,4-dihydroxybenzene, 2-chloro-1,3-di-hydroxybenzene, 1,2-dichloro-3,5-dihydroxy-4-methylbenzene, 1,5-dichloro-2,4-dihydroxy-benzene, 1,3-dihydroxy-2-methylbenzene, 3,4-methylenedioxy-phenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxyindoline, 5-hydroxyindole, 6-hydroxyindole, 7-hydroxyindole and 2,3-indolindione.

Although the advantageous properties of the above-described diaminobenzene derivative compounds of formula (I) can obviously be obtained when the diaminobenzene derivative compounds of formula (I) are used alone, it is understandably also possible to use the diaminobenzene derivative compounds of formula (I) together with known developer substances, such as 1,4-diaminobenzene, 2,5-diaminotoluene, 2,5-diaminophenyl-ethyl alcohol, 4-aminophenol and its derivatives, especially 4-amino-3-methylphenol, 4,5-diaminopyrazole derivative compounds, such as 4,5-diamino-1-(2-hydroxyethyl)pyrazole, or tetraaminopyrimidienes.

The coupler and developer substances can be contained in the dye compositions according to the invention individually, or in mixtures with each other. The total amount of coupler substances and developer substances in the dye composition according to the invention (relative to the total amount of the dye composition) is from about 0.005 to 20 percent by weight respectively, preferably from about 0.01 to 5.0 percent by weight and especially preferably from 0.1 to 2.5 percent by weight.

The total amount of the combination of developer and coupler substances in the dye composition described here is preferably from about 0.01 to 20 percent by weight, especially preferably from about 0.02 to 10 percent by weight, and most preferably from 0.2 to 6.0 percent by weight. The developer and coupler substances are used generally in equimolar amounts, however it is not disadvantageous when the developer substances are present in a certain excess or deficiency.

The dye compositions according to the invention can also contain certain other dye ingredients, for example 6-amino-2-methylphenol and 2-amino-5-methylphenol, as well as conventional direct-dyeing dye compounds, such as triphenyl-methane dye compounds, such as 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-2", 5"-cyclohexadien-1"-yliden)methyl]-2-methylaminobenzene monohydrochloride (C.I. 42 520); aromatic nitro dye compounds, such as 4-(2'-hydroxyethyl)amino-nitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-[(2'-ureidoethyl)amino-4-nitrobenzene; azo dye compounds, such as 6-[(41-aminophenyl)azo]-5-hydroxynapththalen-1-sulfonic acid sodium salt (C.I. 14 805) and dispersion dye compounds, such as 1,4-diaminoanthraquinone and 1,4,5,8 tetraaminoanthraquinone. These dye compounds can be contained in the dye composition of the invention in an amount of from about 0.1 to 4.0 percent by weight.

Understandably the coupler substances and the developer substances as well as the other dye compounds, in so far as they are bases, can also be used in the form of their physiologically compatible salts with organic or inorganic acids, such as hydrochloric acid or sulfuric acid, or, in so art as they have aromatic OH groups, in the form of their salts with bases, such as alkali phenolates.

Moreover cosmetic additive ingredients, which are commonly used in compositions for dyeing hair, can be used in the dye compositions according to the invention, for example antioxidants, such as ascorbic acid, thioglycolic acid or sodium sulfite, and perfume oils, complex formers, wetting agents, emulsifiers, thickeners and care materials. The form of the dye compositions according to the invention can be, for example, a solution, especially an aqueous or aqueous-alcoholic solution. However the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol; wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzenesulfonates, alkyltrimethylammonium salts, aklylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil and fatty acids, as well as care materials, such as cationic resins, lanolin derivatives, cholesterol, pantothenic acids and betaine. The above-mentioned conventional cosmetic ingredients are used in amounts suitable for their purposes. For example the wetting agents and emulsifiers are used in concentrations of from about 0.5 to 30 percent by weight, the thickeners are used in an amount of from about 0.1 to 25 percent by weight and the care materials are used in concentrations of from about 0.1 to 5.0 percent by weight.

The dye compositions according to the invention can be weakly acidic, neutral or alkaline according to their composition. The compositions especially have pH values of from 6.8 to 11.5. Their pH can be adjusted in the basic range with ammonia. Also organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair dye composition for dyeing hair one mixes the above-described dye compositions according to the invention with an oxidizing agent immediately prior to use and applies a sufficient amount of the mixture to the hair, according to the hair abundance, generally from about 60 to 200 grams.

Principally hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Air oxygen can also be used as the oxidizing agent. If a 6 percent hydrogen peroxide solution is used as oxidizing agent, the weight ratio of hair dye composition and oxidizing agent is 5:1 to 1:2, but preferably 1:1. Larger amounts of oxidizing agent are used above all with larger dye concentrations in the hair dye composition, or when at the same time a strong bleaching of the hair is desired. The mixture of the oxidizing agent and the dye composition of the invention is allowed to act on the hair for about 10 to 45 minutes, preferably 30 minutes, at 15 to 50 degrees Celsius, the hair is rinsed with water and dried. If necessary it is washed with a shampoo and eventually after-rinsed with a weak organic acid, such as citric acid or tartaric acid. Subsequently the hair is dried.

The hair dye composition according to the invention with a content of diaminobenzene derivative compounds of formula (I) as developer substances permits hair dyeing with outstanding color fastness, especially light fastness, fastness to washing and fastness to rubbing. The dye composition according to the invention provides a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of gray, chemically not-previously damaged hair without problems.

The diaminobenzene derivative compounds of formula (I) are soluble in water and permit dyeing with higher intensities and outstanding color fastness, especially light fastness, fastness to washing and fastness to rubbing. They have outstanding storage stability, especially as ingredients of the above-described dye compositions.

The subject matter of the invention also includes new diaminobenzene derivative compounds of the formula (I):

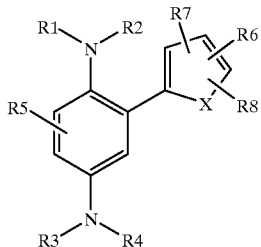

wherein X represents oxygen, sulfur, selenium or N—R9;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the $R_1$ to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 and R8 each represents, independently of each other, hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 represents hydrogen, a halogen atom, a $C_1$- to $C_6$-alkyl group or a —C(O)H group;

R9 represents hydrogen, a $C_1$- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11, R13 and R16 each, independently of each other, represents hydrogen or a $C_1$- to $C_4$-alkyl group;

R12 represents an amino group or a nitrile group;

R14, R17 and R18 each, independently of each other, represent hydrogen, a hydroxy group, a $C_1$- to $C_4$-alkyl group a $C_1$- to $C_4$-hydroxyalkyl group, a $C_3$- to $C_4$-dihydroxyalkyl group or a group of formula (II):

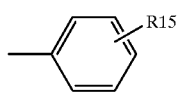

and R15 represents hydrogen, an amino group or a hydroxy group, with the proviso that if X represents oxygen and both R1 and R2 represent a methyl group at least one of the groups R3 to R8 is not hydrogen, or their physiologically compatible water-soluble salts.

Preferred compounds of formula (I) include those in which (i) one or more of the groups R5, R6, R7 and R8 are hydrogen and/or (ii) R1, R2, R3 and R4 are simultaneously hydrogen and/or (iii) R7 is hydrogen and R6 is hydrogen, —C(O)H, —C(O)CH$_3$, $C_1$–$C_4$-alkyl or $C_1$–$C_4$-hydroxyalkyl (particularly R6=R7=hydrogen).

Particularly the following compounds are named: 2,5-diamino-1-(2-thienyl)benzene; 2,5-diamino-1-(2-furyl) benzene; 2,5-diamino-1-(3-acetyl-2-thienyl)benzene; 2,5-diamino-1-(3-chloro-2-thienyl)benzene; 2,5-diamino-1-(1H-pyrrol-2-yl)benzene; 2,5-diamino-1-(3-methyl-2-thienyl)-benzene; 2,5-diamino-1-(5-methyl-2-thienyl) benzene; 2,5-diamino-1-(3-nitro-2-thienyl)benzene; 2-dimethylamino-5-amino-1-(2-thienyl)benzene; 2-pyrrolidino-5-amino-1-(2-thienyl)-benzene, 2-Di(2-hydroxyethyl)amino-5-amino-1-(2-thienyl)-benzene, 2-(2-hydroxyethyl)amino-5-amino-1-(2-thienyl)-benzene, 2-(2-methoxyethyl)amino-5-amino-1-(2-thienyl)benzene, 2-(2,3-dihydroxypropyl)amino-5-amino-1-(2-thienyl)benzene, 2,5-diamino-4-methoxy-1-(2-thienyl)benzene, 2,5-diamino-4-methyl-1-(2-thienyl)benzene, 2,5-diamino-1-(3-chloro-2-thienyl)benzene, 2,5-diamino-1-(1-methylpyrrol-2-yl)-benzene and 2,5-diamino-1-(3-formyl-2-thienyl)benzene.

The new diaminobenzene derivative compounds of formula I according to the invention can be made by known synthesis methods, for example the methods in the following examples or in an analogous manner to the methods described in European Patent Application EP-OS 0 604 353 for synthesis of 4-N,N-dimethylamino-3-(2-furyl)aniline.

The following examples should serve to illustrate the invention, but details present in these examples should not be considered as further limiting the following appended claims, unless they are explicitly included in the following appended claims.

EXAMPLES

Example 1

Synthesis of p-diaminobenzenes of Formula I (General Synthetic Recipe)

A. Synthesis of 2,5-tert-butyloxycarbonylaminobromobenzene 15.65 g (0.07 mol)bromo-p-phenylenediamine hydrochloride and 32.7 g (0.15 mol)di-tert.-butyl-dicarbonate are dissolved in a mixture of 250 ml 2N sodium hydroxide and 250 ml trifluorotoluene and heated at 45° C. This reaction mixture is stirred from 3 days. Then 30 g (0.14 mol) di-tert.butyl dicarbonate is added stepwise. Subseqeuntly the organic layer is separated and the aqueous phase is extracted twice with 100 ml dichloromethane. The combined extracts are evaporated to dryness and the residue is taken up in 200 ml of hexane. The precipitate is filtered and washed with 50 ml hexane. 18.6 g (82% of theoretical) of 2,5-tert.-butyloxycarbonylaminobromobenzene is obtained with a melting point of 130° C.

B. Synthesis of 2,5-diamino-1-(2-thienyl)benzenes and 2,5-diamino-1-(2-furyl)benzenes 3.3 g (0.01 mol) 2,5-tert.-butyloxycarbonylaminobromobenzene from step A and 0.013 mol of the corresponding boric acid are dissolved in 70 ml of 1,2-dimethyoxyethane under argon. Subsequently 0.5 g tetrakis(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with petroleum ether/acetic acid ethyl ester (9:1). The product obtained in this way is heated to 50° C. in 40 ml ethanol. Then 15 ml of a 2.9 molar ethanolic hydrochloric acid solution is added dropwise to make the hydrochloride salt. The precipitate is filtered, washed twice with 10 ml ethanol and then dried.

a.2,5-diamino-1-(2-thienyl)benzene dihydrochloride

Boric acid used: thiophen-2-boric acid Yield: 1.6 g (61% of theoretical) Melting Point: 235° C. (decomposes) (colorless crystals) CHN Analysis:

| $C_{10}H_{12}N_2Cl_2S$ | % C | % H | % N |
|---|---|---|---|
| Calculated | 45.64 | 4.60 | 10.64 |
| Found | 45.89 | 4.68 | 10.64 | b. 2,5-diamino-1-(2-furyl)benzene dihydrochloride
   Boric acid used: furan-2-boric acid
   Yield: 1.6 g (63% of theoretical)
   Melting Point: 245° C. (decomposes) (colorless crystals)
CHN Analysis:

| $C_{10}H_{12}N_2Cl_2O$ | % C | % H | % N |
|---|---|---|---|
| Calculated | 48.60 | 4.89 | 11.34 |
| Found | 48.78 | 4.48 | 11.31 | c. 2,5-diamino-1-(3-acetyl-2-thienyl)benzene dihydrochloride
   Boric acid used: (3-acetyl-2-thienyl)-boric acid
   Yield: 1.98 g (65% of theoretical)
   Melting Point: 245° C. (decomposes) (colorless crystals)
CHN Analysis:

| $C_{12}H_{14}N_2OCl_2S$ | % C | % H | % N |
|---|---|---|---|
| Calculated | 47.22 | 4.62 | 9.18 |
| Found | 48.59 | 4.69 | 8.58 | d. 2,5-diamino-1-(3-chloro-2-thienyl)benzene dihydrochloride
   Boric acid used: (3-chloro-2-thienyl)-boric acid
   Yield: 1.7 g (56% of theoretical)
   Melting Point: 245° C. (decomposes) (colorless crystals)
CHN Analysis:

| $C_{10}H_9N_2ClS$ | % C | % H | % N |
|---|---|---|---|
| Calculated | 40.45 | 3.73 | 9.41 |
| Found | 40.56 | 3.81 | 9.41 | e. 2,5-diamino-1-(1H-pyrrol-2-yl)benzene dihydrochloride
   Boric acid used: 1-tert-butoxycarbonyl-pyrrol-2-boric acid
   Yield: 0.32 g (13% of theoretical)
   Melting Point: 245° C. (decomposes)(colorless crystals)
CHN Analysis:

| $C_{10}H_{13}N_3Cl_2$ | % C | % H | % N |
|---|---|---|---|
| Calculated | 48.80 | 5.32 | 17.07 |
| Found | 48.68 | 4.98 | 16.47 |

C. Synthesis of N,N'-bis-(tert.-butoxycarbonyl)-2,5-diamino-1-phenylboric acid.
   N,N'-bis-(tert.-butoxycarbonyl)-2,5-diamino-1-phenylboric acid is made by reaction of N,N'-bis-(tert.-butoxycarbonyl)-2,5-diamino-1-bromobenzene with tert.-butyl lithium and trimethyl-borate. The experimental prescription for this synthetic method is described in the article by J. M. Tour and J. J. Lamba in J. Am. Chem. Soc. 1994, 116, p. 11723.

D. Synthesis of 2,5-Diamino-1-(2-thienyl)benzenes and 2,5diamino-1-(2-furyl)-benzenes
   0.035 g (0.0001 mol) 2,5-tert.-butyloxycarbonylamino-1-phenyl-boric acid from step C and 0.00015 mol of the corresponding bromo derivatives are dissolved in 10 ml 1,2-dimethoxyethane under argon. Then 0.005 g tetrakis(triphenylphosphine)-pallidium (0.000005 mol) and 0.13 ml of 2 N potassium carbonate solution are added dropwise and the reaction mixture is heated to 80° C. After halting the reaction the reaction mixture is poured into 10 ml of acetic acid ethyl ester, the organic phase is extracted with dilute sodium hydroxide and then dried with magnesium sulfate. The solvent is distilled off with a rotary evaporator and the residue is purified on silica gel with petroleum ether/acetic acid ethyl ester (9:1). The product so obtained is heated to 50° C. in 4 ml of ethanol. Finally 1.5 ml of a 2.9 molar ethanolic hydrochloric acid solution is added dropwise to make the hydrochloride. The precipitate is filtered off, washed twice with 1 ml ethanol and then dried.

a. 2,5-diamino-1-(3-methyl-2-thienyl)benzene dihydrochloride
   Bromo derivative used: 2-bromo-5-methylthiophene
   Yield: 0.025 g (71% theoretical)
   Melting Point: 245° C. (decomposes) (colorless crystals)

b. 2,5-diamino-1-(5-methyl-2-thienyl benzene dihydrochloride
   Bromo derivative used: 2-bromo-3-methylthiophene
   Yield: 0.025 g (80% theoretical)
   Melting Point: 245° C. (decomposes) (colorless crystals)

c. 2,5-diamino-1-(3-nitro-2-thienyl)benzene dihydrochloride
   Bromo derivative used: 2-bromo-5-nitrothiophene
   Yield: 0.025 g (71% theoretical)
   Mass spectra $M^+$ 205(100)

Example 2

Synthesis of 2-N-substituted -amino-5-amino-1-(2-thienyl)benzenes (General Synthesis)

A. Synthesis of 2-fluoro-5-nitro -1-(2-thienyl)benzetie
   1.75 g (0.01 mol) 1-chloro-2-fluoro-5-nitrobenzene and 0.013 mol thiophen-2-boric acid are dissolved in 70 ml 1,2-dimethoxyethane under argon. Subsequently 0.5 g tetrakis-(triphenylphosphen)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). 1.24 g (56% of theoretical) of the product, 2-fluoro-5-nitro-1-(2-thienyl)benzene, were obtained with a melting point of 65° C.

B. Synthesis of 2-N-substituted-2-amino-5-amino-1-(2-thienyl)-Benzenes
   0.56 g (0.0025 mol)2-fluoro-5-nitro-1-(2-thienyl)benzene from step A and 5 ml of the corresponding amine are dissolved in ethanol. Subsequently the reaction mixture is heated to 80° C. After halting the reaction the reaction mixture is poured into 50 g of ice, extracted with acetic acid ethyl ester and then dried with magnesium sulfate. The solvent is distilled off in a rotary evaporator and the residue is purified on silica gel with dichloromethane/ethanol (50:1). The product thus obtained is dissolved in 30 ml ethanol and hydrogenated under addition of 100 mg of a palladium-activated carbon catalyst (10%) at 50° C. After up-take of the required amount of hydrogen the product-containing mixture is filtered to remove the catalyst and the solvent is distilled of in a rotary evaporator. Then 5 ml of 2.9 molar ethanolic hydrochloric acid solution is added dropwise to prepare the hydrochloride salt. The precipitate is filtered off, washed twice with 10 ml of ethanol and then dried.

a. 2-dimethylamino-5-amino-1-(2-thienyl)benzene dihydrochloride

Amine used: dimethylamine
Yield: 0.58 g (77% theoretical)
Melting point: 232° C. (decomposes) (colorless crystals)
CHN Analysis:

| $C_{12}H_{16}N_2Cl_2S$ | % C | % H | % N |
|---|---|---|---|
| Calculated: | 49.48 | 5.54 | 9.61 |
| Found: | 48.65 | 5.48 | 9.39 | b. 2-pyrrolidino-5-amino-1-(2-thienyl)benzene dihydrochloride

Amine used: pyrrolidine
Yield: 0.69 g (69% theoretical)
Melting point: 205° C. (decomposes) (colorless crystals)
CHN Analysis:

| $C_{14}H_{18}N_2Cl_2S$ | % C | % H | % N |
|---|---|---|---|
| Calculated: | 52.99 | 5.72 | 8.83 |
| Found: | 52.58 | 5.93 | 8.59 | c. 2-di(2-hydroxyethyl)amino-5-amino-1-(2-thienyl)benzene dihydrochloride

Amine used: diethanolamine
Yield: 0.76 g (87% theoretical)
Melting point: 208° C. (decomposes) (colorless crystals)
CHN Analysis:

| $C_{14}H_{20}N_2O_2Cl_2S$ | C % | % H | % N |
|---|---|---|---|
| Calculated: | 47.86 | 5.74 | 7.97 |
| Found: | 47.65 | 5.67 | 7.83 | d. 2-(2-hydroxyethyl)amino-5-amino-1-(2-thienyl)benzene dihydrochloride

Amine used: ethanolamine
Yield: 0.95 g (87% theoretical)
Melting point: 208° C. (decomposes) (colorless crystals)
CHN Analysis:

| $C_{12}H_{16}N_2OCl_2S$ | C % | % H | % N |
|---|---|---|---|
| Calculated: | 46.91 | 5.25 | 9.12 |
| Found: | 47.1 | 5.32 | 9.16 | e. 2-(2-methoxyethyl)amino-5-amino-1-(2-thienyl)benzene dihydrochloride

Amine used: 2-methoxyethylamine
Yield: 0.60 g (79% theoretical)
Melting point: 208° C(decomposes) (colorless crystals)
CHN Analysis:

| $C_{13}H_{18}N_2OCl_2S$ | C % | % H | % N |
|---|---|---|---|
| Calculated: | 48.60 | 5.65 | 8.72 |
| Found: | 51.00 | 6.37 | 8.08 | f. 2-(2,3-dihydroxypropyl)amino-5-amino-1-(2-thienyl)benzene dihydrochloride

Amine used: 2,3-dihydroxypropylamine
Yield: 0.71 g (85% theoretical)
Melting point: 208° C.(decomposes) (colorless crystals)
CHN Analysis:

| $C_{13}H_{18}N_2O_2Cl_2S$ | C % | % H | % N |
|---|---|---|---|
| Calculated: | 46.3 | 5.38 | 8.31 |
| Found: | 48.80 | 6.21 | 8.20 |

Example 3

Synthesis of 2,5-diamino-4-methyl-1-(2-thienyl)benzene 1.87 g (0.01 mol) 5-chloro-2-methyl-4-nitroaniline and 0.013 mol thiophen-2-boric acid are dissolved in 70 ml 1,2-dimethoxyethane under argon. Subsequently 0.5 g tetrakis-(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). The product thus obtained is dissolved in 30 ml ethanol and hydrogenated under addition of 100 mg of a palladium-activated carbon catalyst (10%) at 50° C. After up-take of the required amount of hydrogen the product-containing mixture is filtered to remove the catalyst and the solvent is distilled off in a rotary evaporator. Then 5 ml of 2.9 molar ethanolic hydrochloric acid solution is added dropwise to prepare the hydrochloride salt. The precipitate is filtered off, washed twice with 10 ml of ethanol and then dried.

Yield: 0.2 g (10% theoretical)
CHN Analysis:

| $C_{11}H_{14}N_2Cl_2S$ | C % | % H | % N |
|---|---|---|---|
| Calculated: | 47.66 | 5.09 | 10.11 |
| Found: | 44.64 | 5.58 | 10.57 |

Example 4

Synthesis of 2,5-diamino-4-methoxy-1-(2-thienyl)benzene 1.87 g (0.01 mol) 5-chloro-2-methoxy-4-nitroaniline and 0.013 mol thiophen-2-boric acid are dissolved in 70 ml 1,2-dimethoxyethane under argon. Subsequently 0.5 g tetrakis-(triphenylphosphine)palladium (0.0005 mol) and 13 ml 2N potassium carbonate are added and the resulting reaction mixture is heated to 80° C. After termination of the reaction, the reaction mixture is poured into 100 ml acetic acid ethyl ester, the organic phase is extracted with dilute sodium hydroxide and then dried with magnesium sulfate. The solvent is distilled off in a rotary evaporator and the residue is purified on silica gel with hexane/acetic acid ethyl ester (20:1). The product thus obtained is dissolved in 30 ml ethanol and hydrogenated under addition of 100 mg of a palladium-activated carbon catalyst (10%) at 50° C. After up-take of the required amount of hydrogen the product-containing mixture is filtered to remove the catalyst and the solvent is distilled of in a rotary evaporator. Then 5 ml of 2.9 molar ethanolic hydrochloric acid solution is added dropwise to prepare the hydrochloride salt. The precipitate is filtered off, washed twice with 10 ml of ethanol and then dried.

Yield: 0.53 g (30% theoretical)
CHN Analysis:

| $C_{11}H_{14}N_2Cl_2OS$ | C % | % H | % N |
|---|---|---|---|
| Calculated: | 45.06 | 4.81 | 9.55 |
| Found: | 42.92 | 5.29 | 9.26 |

EXAMPLES 5 TO 71

HAIR DYE COMPOSITIONS

Hair Dye Solutions were prepared having the following composition:

| 0.0125 mol | developer substance of formula I according to Table I |
|---|---|
| 0.0125 mol | coupler substance according to Table I |
| 10.0 g | potassium oleate (8% aqueous solution) |
| 10.0 g | ammonia (22 percent aqueous solution) |
| 10.0 g | isopropanol |
| 0.3 g | ascorbic acid |
| to 100.0 g | water |

30 g of the above-described dye solution were mixed immediately prior to use with 30 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table I.

TABLE I

HAIR DYEING COMPOSITIONS

| EXAMPLE | DEVELOPER OF FORMULA I | COUPLER | COLOR OBTAINED |
|---|---|---|---|
| 5 | 2,5-diamino-1-(2-thienyl)benzene*2HCl | 2-amino-4-(2'-hydroxy-ethyl)amino-anisole sulfate | Dark blue |
| 6 | 2,5-diamino-1-(2-thienyl)benzene*2HCl | m-aminophenol | Dark gray |
| 7 | 2,5-diamino-1-(2-thienyl)benzene*2HCl | 5-amino-2-methyl-phenol | Red |
| 8 | 2,5-diamino-1-(2-thienyl)benzene*2HCl | Resorcinol | Dark blond |

TABLE I-continued

HAIR DYEING COMPOSITIONS

| EXAMPLE | DEVELOPER OF FORMULA I | COUPLER | COLOR OBTAINED |
|---|---|---|---|
| 9 | 2,5-diamino-1-(2-thienyl)benzene*2HCl | 1-chloro-2,4-dihydroxybenzene | Dark blond |
| 10 | 2,5-diamino-1-(2-thienyl)benzene*2HCl | 1,3-diaminobenzene | Dark blue |
| 11 | 2,5-diamino-1-(2-thienyl)benzene*2HCl | 1-naphthol | Dark red-blue |
| 12 | 2,5-diamino-1-(2-thienyl)benzene*2HCl | 5-hydroxy-1,3-benzo-dioxole | Dark blond |
| 13 | 2,5-diamino-1-(2-thienyl)benzene*2HCl | 3-amino-2-chloro-6-methylphenol | Dark red-blue |
| 14 | 2,5-diamino-1-(2-thienyl)benzene*2HCl | 3-amino-6-methoxy-2-(methylamino)-pyridine.2HCl | Dark blue |
| 15 | 2,5-diamino-1-(2-thienyl)benzene*2HCl | 1,3-Di-(2,4-diamino-phenoxy)propane*4HCl | Dark blue |
| 16 | 2,5-diamino-1-(2-thienyl)benzene*2HCl | 1,3-diamino-4-(2-hydroxyethoxy)-benzene | Dark blue |
| 17 | 2,5-diamino-1-(2-thienyl)benzene*2HCl | 1,3-dihydroxy-2-methylbenzene | blond |
| 18 | 2,5-diamino-1-(2-thienyl)benzene*2HCl | 5-((2-hydroxyethyl)-amino)-2-methylphenol | Red |
| 19 | 2,5-diamino-1-(2-thienyl)benzene*2HCl | 1,5-dihydroxy-naphthalene | Blue |
| 20 | 2,5-diamino-1-(2-thienyl)benzene*2HCl | 1,5-dihydroxy-naphthalene | Red blue |
| 21 | 2,5-diamino-1-(2-thienyl)benzene*2HCl | 5-(2-hydroxyethyl)-amino-1,3-benzo-dioxole*HCl | Dark blond |
| 22 | 2,5-diamino-1-(2-thienyl)benzene*2HCl | Acetic acid-(2-methyl-Naphthalen-1-yl)ester | Violet |
| 23 | 2,5-diamino-1-(2-thienyl)benzene*2HCl | 5,6-dihydroxy-1H-indole | Blond |
| 24 | 2,5-diamino-1-(2-furyl)benzene*2HCl | 2-amino-4-(2'-hy-droxy-ethyl)amino an-isole sulfate | Dark blue |
| 25 | 2,5-diamino-1-(2-furyl)benzene*2HCl | m-aminophenol | Dark gray |
| 26 | 2,5-diamino-1-(2-furyl)benzene*2HCl | 5-amino-2-methyl-phenol | Red |
| 27 | 2,5-diamino-1-(2-furyl)benzene*2HCl | Resorcinol | Dark blond |
| 28 | 2,5-diamino-1-(3-acetyl-2-thienyl)benzene*2HCl | 2-amino-4-(2'-hydroxy-ethyl)amino-anisole sulfate | Dark blue |
| 29 | 2,5-diamino-1-(3-acetyl-2-thienyl)benzene*2HCl | m-aminophenol | Dark gray |
| 30 | 2,5-diamino-1-(3-acetyl-2-thienyl)benzene*2HCl | 5-amino-2-methyl-phenol | Red |
| 31 | 2,5-diamino-1-(3-acetyl-2-thienyl)benzene*2HCl | Resorcinol | Dark blond |
| 32 | 2,5-diamino-1-(3-chloro-2-thienyl)benzene*2HCl | 2-amino-4-(2'-hydroxy-ethyl)amino-anisole sulfate | Dark blue |
| 33 | 2,5-diamino-1-(3-chloro-2-thienyl)benzene*2HCl | m-aminophenol | Dark gray |
| 34 | 2,5-diamino-1-(3-chloro-2-thienyl)benzene*2HCl | 5-amino-2-methyl-phenol | Red |
| 35 | 2,5-diamino-1-(3-chloro-2-thienyl)benzene*2HCl | Resorcinol | Dark blond |
| 36 | 2-Di(2-hydroxyethyl)-amino-5-amino-1-(2-thienyl)benzene*2HCl | 2-amino-4-(2'-hydroxy-ethyl)amino-anisole sulfate | Blue red |
| 37 | 2-Di(2-hydroxyethyl)-amino-5-amino-1-(2-thienyl)benzene*2HCl | 3-aminophenol | Gray |
| 38 | 2-Di(2-hydroxyethyl)-amino-5-amino-1-(2-thienyl)benzene*2HCl | 5-amino-2-methyl-phenol | Red |
| 39 | 2-Di(2-hydroxyethyl)-amino-5-amino-1-(2-thienyl)benzene*2HCl | 1,3-dihydroxybenzene | Blond |

TABLE I-continued

HAIR DYEING COMPOSITIONS

| EXAMPLE | DEVELOPER OF FORMULA I | COUPLER | COLOR OBTAINED |
|---|---|---|---|
| 40 | 2-pyrrolidino-5-amino-1-(2-thienyl)benzene*2HCl | 2-amino-4-(2'-hydroxy-ethyl)amino-anisole sulfate | Blue |
| 41 | 2-pyrrolidino-5-amino-1-(2-thienyl)benzene*2HCl | 3-aminophenol | Gray |
| 42 | 2-pyrrolidino-5-amino-1-(2-thienyl)benzene*2HCl | 5-amino-2-methylphenol | Red |
| 43 | 1,3-dihydroxybenzene-2-amino-4-(2-hydroxy-ethyl)amino anisole sulfate | 1,3-dihydroxybenzene | Blond |
| 44 | 2-dimethylamino-5-amino-1-(2-thienyl)benzene*2HCl | 2-amino-4-(2'-hydroxy-ethyl)amino-anisole sulfate | Blue |
| 45 | 2-dimethylamino-5-amino-1-(2-thienyl)benzene*2HCl | 3-aminophenol | Gray |
| 46 | 2-dimethylamino-5-amino-1-(2-thienyl)benzene*2HCl | 5-amino-2-methylphenol | Red |
| 47 | 2-dimethylamino-5-amino-1-(2-thienyl)benzene*2HCl | 1,3-dihydroxybenzene | Blond |
| 48 | 2-(2'-hydroxyethyl)amino-5-amino-1-(2-thienyl)-benzene*2HCl | 2-amino-4-(2'-hydroxy-ethyl)amino-anisole sulfate | Blue |
| 49 | 2-(2'-hydroxyethyl)amino-5-amino-1-(2-thienyl)-benzene*2HCl | 3-aminophenol | Gray |
| 50 | 2-(2'-hydroxyethyl)amino-5-amino-1-(2-thienyl)-benzene*2HCl | 5-amino-2-methylphenol | Red |
| 51 | 2-(2'-hydroxyethyl)amino-5-amino-1-(2-thienyl)-benzene*2HCl | 1,3-dihydroxybenzene | Blond |
| 52 | 2-(2'-methoxyethyl)amino-5-amino-1-(2-thienyl)-benzene*2HCl | 2-amino-4-(2'-hydroxy-ethyl)amino-anisole sulfate | Blue |
| 53 | 2-(2'-methoxyethyl)amino-5-amino-1-(2-thienyl)-benzene*2HCl | 3-aminophenol | Gray |
| 54 | 2-(2'-methoxyethyl)-amino-5-amino-1-(2-thienyl)-benzene*2HCl | 5-amino-2-methylphenol | Red |
| 55 | 2-(2'-methoxyethyl)amino-5-amino-1-(2-thienyl)-benzene*2HCl | 1,3-dihydroxybenzene | blond |
| 56 | 2-(2,3-dihydroxypropyl)-5-amino-1-(2-thienyl)-benzene*2HCl | 2-amino-4-(2'-hydroxy-ethyl)amino-anisole sulfate | Blue |
| 57 | 2-(2,3-dihydroxypropyl)-5-amino-1-(2-thienyl)-benzene*2HCl | 3-aminophenol | Gray |
| 58 | 2-(2,3-dihydroxypropyl)-5-amino-1-(2-thienyl)-benzene*2HCl | 5-amino-2-methylphenol | Red |
| 59 | 2-(2,3-dihydroxypropyl)-5-amino-1-(2-thienyl)-benzene*2HCl | 1,3-dihydroxybenzene | Blond |
| 60 | 2,5-diamino-1-(1H-pyrrol-2-yl)benzene*2HCl | 2-amino-4-(2'-hydroxy-ethyl)amino-anisole sulfate | Blue |
| 61 | 2,5-diamino-1-(1H-pyrrol-2-yl)benzene*2HCl | 3-aminophenol | Grey |
| 62 | 2,5-diamino-1-(1H-pyrrol-2-yl)benzene*2HCl | 5-amino-2-methylphenol | Red |
| 63 | 2,5-diamino-1-(1H-pyrrol-2-yl)benzene*2HCl | 1,3-dihydroxybenzene | Blond |
| 64 | 2,5-diamino-4-methoxy-1-(2-thienyl)benzene*2HCl | 2-amino-4-(2'-hydroxy-ethyl)amino-anisole sulfate | Blue |
| 65 | 2,5-diamino-4-methoxy-1-(2-thienyl)benzene*2HCl | 3-aminophenol | Blue-green |
| 66 | 2,5-diamino-4-methoxy-1-(2-thienyl)benzene*2HCl | 5-amino-2-methylphenol | Violet |
| 67 | 2,5-diamino-4-methoxy-1-(2-thienyl)benzene*2HCl | 1,3-dihydroxybenzene | Violet |
| 68 | 2,5-diamino-4-methyl-1-(2-thienyl)benzene*2HCl | 2-amino-4-(2'-hydroxy-ethyl)amino-anisole sulfate | Blue |
| 69 | 2,5-diamino-4-methyl-1-(2-thienyl)benzene*2HCl | 3-aminophenol | Gray |
| 70 | 2,5-diamino-4-methyl-1-(2-thienyl)benzene*2HCl | 5-amino-2-methylphenol | Red |
| 71 | 2,5-diamino-4-methyl-1-(2-thienyl)benzene*2HCl | 1,3-dihydroxybenzene | blond |

EXAMPLES 72 TO 83

HAIR DYE COMPOSITIONS

Hair Dye Solutions were prepared having the following composition:

| | | |
|---|---|---|
| 0.0000125 mol | developer substance of formula I according to Table II | |
| 0.0000125 mol | coupler substance according to Table II | |
| 0.01 g | potassium oleate(8% aqueous solution) | |
| 0.01 g | ammonia (22 percent aqueous solution) | |
| 0.01 g | ethanol | |
| 0.003 g | ascorbic acid | |
| to 100.0 g | water | |

1 g of the above-described dye solution were mixed immediately prior to use with 1 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table II.

TABLE II

HAIR DYEING COMPOSITIONS

| EXAMPLE | DEVELOPER OF FORMULA I | COUPLER | COLOR OBTAINED |
|---|---|---|---|
| 72 | 2,5-diamino-1-(3-methyl-2-thienyl)benzene*2HCl | 1,3-diamino-4-(2-hydroxyethoxy)-benzene | Dark blue |
| 73 | 2,5-diamino-1-(3-methyl-2-thienyl)benzene*2HCl | 1-naphthol | Blue |
| 74 | 2,5-diamino-1-(3-methyl-2-thienyl)benzene*2HCl | 5-amino-2-methyl-phenol | Red |
| 75 | 2,5-diamino-1-(3-methyl-2-thienyl)benzene*2HCl | Resorcinol | Dark blond |

TABLE II-continued

HAIR DYEING COMPOSITIONS

| EXAMPLE | DEVELOPER OF FORMULA I | COUPLER | COLOR OBTAINED |
|---|---|---|---|
| 76 | 2,5-diamino-1-(5-methyl-2-thienyl)benzene*2HCl | 1,3-diamino-4-(2-hydroxyethoxy)-benzene | Dark blue |
| 77 | 2,5-diamino-1-(5-methyl-2-thienyl)benzene*2HCl | 1-naphthol | Blue |
| 78 | 2,5-diamino-1-(5-methyl-2-thienyl)benzene*2HCl | 5-amino-2-methyl-phenol | Red |
| 79 | 2,5-diamino-1-(5-methyl-2-thienyl)benzene*2HCl | Resorcinol | Dark blond |
| 80 | 2,5-diamino-1-(3-nitro-2-thienyl)benzene*2HCl | 1,3-diamino-4-(2-hydroxyethoxy)-benzene | Dark blue |
| 81 | 2,5-diamino-1-(3-nitro-2-thienyl)benzene*2HCl | 1-naphthol | Blue |
| 82 | 2,5-diamino-1-(3-nitro-2-thienyl)benzene*2HCl | 5-amino-2-methyl-phenol | Red |
| 83 | 2,5-diamino-1-(3-nitro-2-thienyl)benzene*2HCl | Resorcinol | Dark-blond |

EXAMPLES 84 TO 124

HAIR DYE COMPOSITIONS

Hair Dye Solutions were prepared having the following composition:

| | | |
|---|---|---|
| 0.000625 mol | developer substance of formula I according to Table III | |
| 0.000625 mol | additional developer substance according to Table III | |
| 0.001250 mol | coupler substance according to Table III | |
| 10.0 g | potassium oleate(8% aqueous solution) | |
| 10.0 g | ammonia (22 percent aqueous solution) | |
| 10.0 g | isopropanol | |
| 0.3 g | ascorbic acid | |
| to 100.0 g | water | |

30 g of the above-described dye solution were mixed immediately prior to use with 30 g of 6 percent hydrogen peroxide solution. Then the mixture was applied to bleached hair. After an acting time of 30 minutes at 40° C., the hair was rinsed with water, washed with a shampoo and dried. The resulting colors for the dyeing hair are summarized in the following Table III.

TABLE III

HAIR DYEING COMPOSITIONS

| EXAMPLE | DEVELOPER OF FORMULA I | COUPLER | COLOR OBTAINED |
|---|---|---|---|
| 84 | 2,5-diamino-1-(2-thienyl)-benzene*2HCl/1,4-diaminobenzene | 2-amino-4-(2'-hydroxy-ethyl)amino-anisole sulfate | Dark blue |
| 85 | 2,5-diamino-1-(2-thienyl)-benzene*2HCl/1,4-diaminobenzene | 1,3-dihydroxy-2-methylbenzene | Blond |
| 86 | 2,5-diamino-1-(2-thienyl)-benzene*2HCl/1,4-diaminobenzene | 5-((2-hydroxy-ethyl)-amino)-1,3-benzo-dioxole*HCl | Dark blond-olive green |
| 87 | 2,5-diamino-1-(2-thienyl)-benzene*2HCl/1,4-diaminobenzene | 5-amino-2-methyl-benzene | Red blue |
| 88 | 2,5-diamino-1-(2-thienyl)-benzene*2HCl/1,4-diaminobenzene | 3-aminophenol | Gray |
| 89 | 2,5-diamino-1-(2-thienyl)-benzene*2HCl/1,4-diaminobenzene | 1,3-diamino-4-(2'-hydroxyethoxy)benzene | Dark blue |
| 90 | 2,5-diamino-1-(2-thienyl)-benzene*2HCl/1,4-diaminobenzene | 1,3-dihydroxybenzene | Blond |
| 91 | 2,5-diamino-1-(2-thienyl)-benzene*2HCl/1,4-diamino-2-methylbenzene | 2-amino-4-(2-hydroxy-ethyl)amino anisole sulfate | Dark blue |
| 92 | 2,5-diamino-1-(2-thienyl)-benzene*2HCl/1,4-diamino-2-methylbenzene | 1,3-dihydroxy-2-methylbenzene | Blond |
| 93 | 2,5-diamino-1-(2-thienyl)-benzene*2HCl/1,4-diamino-2-methylbenzene | 5-((2-hydroxyethyl)-amino)-1,3-benzo-dioxole*HCl | Dark blond-Olive green |
| 94 | 2,5-diamino-1-(2-thienyl)-benzene*2HCl/1,4-diamino-2-methylbenzene | 5-amino-2-methyl-phenol | Violet |
| 95 | 2,5-diamino-1-(2-thienyl)-benzene*2HCl/1,4-diamino-2-methylbenzene | 3-aminophenol | Gray-red |
| 96 | 2,5-diamino-1-(2-thienyl)-benzene*2HCl/1,4-diamino-2-methylbenzene | 1,3-diamino-4-(2'-hydroxyethoxy)benzene | Dark blue |
| 97 | 2,5-diamino-1-(2-thienyl)-benzene*2HCl/1,4-diamino-2-methylbenzene | 1,3-dihydroxybenzene | Blond |
| 98 | 2,5-diamino-1-(2-thienyl)-benzene*2HCl/4-Di(2-hydroxyethyl)amino-aniline sulfate | 2-amino-4-(2'-hydroxy-ethyl)aminoanisole sulfate | Dark blue |
| 99 | 2,5-diamino-1-(2-thienyl)-benzene*2HCl/4-Di(2-hydroxyethyl)amino-aniline sulfate | 1,3-dihydroxy-2-methylbenzene | Brown |
| 100 | 2,5-diamino-1-(2-thienyl)-benzene*2HCl/4-Di(2-hydroxyethyl)amino-aniline sulfate | 5-((2-hydroxyethyl)-amino)-1,3-benzo-dioxole*HCl | Dark blond-Olive green |
| 101 | 2,5-diamino-1(2-thienyl)-benzene*2HCl/4-Di(2-hydroxyethyl)amino-aniline sulfate | 5-amino-2-methyl-phenol | Violet |
| 102 | 2,5-diamino-1-(2-thienyl)-benzene*2HCl/4-Di(2-hydroxyethyl)amino-aniline sulfate | 3-aminophenol | Gray-blue |
| 103 | 2,5-diamino-1-(2-thienyl)-benzene*2HCl/4-Di(2-hydroxyethyl)amino-aniline sulfate | 1,3-diamino-4-(2'-hydroxyethoxy)benzene | Dark blue |
| 104 | 2,5-diamino-1-(2-thienyl)-benzene*2HCl/4-Di(2-hydroxyethyl)amino-aniline sulfate | 1,3-dihydroxybenzene | Blond |
| 105 | 2,5-diamino-1-(2-thienyl)-benzene*2HCl/4-aminophenol | 2-amino-4-(2'-hydroxy-ethyl)amino-anisole sulfate | Violet |
| 106 | 2,5-diamino-1-(2-thienyl)-benzene*2HCl/4-aminophenol | 1,3-dihydroxy-2-methylbenzene | Blond |
| 107 | 2,5-diamino-1-(2-thienyl)-benzene*2HCl/4-aminophenol | 5-((2-hydroxyethyl)-amino)-1,3-benzo-dioxole*HCl | Blond-Olive green |

TABLE III-continued

HAIR DYEING COMPOSITIONS

| EXAMPLE | DEVELOPER OF FORMULA I | COUPLER | COLOR OBTAINED |
|---|---|---|---|
| 108 | 2,5-diamino-1-(2-thienyl)-benzene*2HCl/4-aminophenol | 5-amino-2-methylphenol | Red |
| 109 | 2,5-diamino-1-(2-thienyl)-benzene*2HCl/4-aminophenol | 3-aminophenol | Brown |
| 110 | 2,5-diamino-1-(2-thienyl)-benzene*2HCl/4-aminophenol | 1,3-diamino-4-(2-hydroxyethoxy)-benzene | Dark blue |
| 111 | 2,5-diamino-1-(2-thienyl)-benzene*2HCl/4-aminophenol | 1,3-dihydroxybenzene | Blond |
| 112 | 2,5-diamino-1-(2-thienyl)-benzene*2HCl/2,4,5,6-tetraaminopyrimidine sulfate | 2-amino-4-(2'-hydroxy-ethyl)aminoanisole sulfate | Dark blue |
| 113 | 2,5-diamino-1-(2-thienyl)-benzene*2HCl/2,4,5,6-tetraaminopyrimidine sulfate | 1,3-dihydroxy-2-methylbenzene | Red |
| 114 | 2,5-diamino-1-(2-thienyl)-benzene*2HCl/2,4,5,6-tetraaminopyrimidine sulfate | 5-((2-hydroxyethyl)-amino)-1,3-benzodioxole*HCl | Gray-green |
| 115 | 2,5-diamino-1-(2-thienyl)-benzene*2HCl/2,4,5,6-tetraaminopyrimidine sulfate | 5-amino-2-methylphenol | Violet |
| 116 | 2,5-diamino-1-(2-thienyl)-benzene*2HCl/2,4,5,6-tetraaminopyrimidine sulfate | 3-aminophenol | Brown |
| 117 | 2,5-diamino-1-(2-thienyl)-benzene*2HCl/2,4,5,6-tetraaminopyrimidine sulfate | 1,3-dihydroxybenzene | Bright brown |
| 118 | 2,5-diamino-1-(2-thienyl)-benzene*2HCl/4,5-di-amino-1-(2-hydroxyethyl)-1H-pyrazole sulfate | 2-amino-4-(2'-hydroxy-ethyl)aminoanisole sulfate | Dark violet |
| 119 | 2,5-diamino-1-(2-thienyl)-benzene*2HCl/4,5-di-amino-1-(2-hydroxyethyl)-1H-pyrazole sulfate | 1,3-dihydroxy-2-methyl-benzene | Bright red |
| 120 | 2,5-diamino-1-(2-thienyl)-benzene*2HCl/4,5-di-amino-1-(2-hydroxyethyl)-1H-pyrazole sulfate | 5-((2-hydroxyethyl)-amino)-1,3-benzodioxole*HCl | Brown red |
| 121 | 2,5-diamino-1-(2-thienyl)-benzene*2HCl/4,5-di-amino-1-(2-hydroxyethyl)-1H-pyrazole sulfate | 5-amino-2-methylphenol | Red |
| 122 | 2,5-diamino-1-(2-thienyl)-benzene*2HCl/4,5-di-amino-1-(2-hydroxyethyl)-1H-pyrazole sulfate | 3-aminophenol | Red |
| 123 | 2,5-diamino-1-(2-thienyl)-benzene*2HCl/4,5-di-amino-1-(2-hydroxyethyl)-1H-pyrazole sulfate | 1,3-diamino-4-(2-hydroxyethoxy)-benzene | Violet |
| 124 | 2,5-diamino-1-(2-thienyl)-benzene*2HCl/4,5-di-amino-1-(2-hydroxyethyl)-1H-pyrazole sulfate | 1,3-dihydroxybenzene | Bright Red |

Example 125

HAIR DYE COMPOSITION

A hair dyeing solution having the following composition was prepared:

| | |
|---|---|
| 0.160 g | 2,5-diamino-1-(2-thienyl)benzene*2HCl |
| 0.160 g | 1,4-diamino-2-(2-hydroxyethyl)benzene sulfate |
| 0.137 g | 1,3-dihydroxybenzene |
| 0.100 g | 1,3-dihydroxy-2-methylbenzene |
| 0.100 g | 2-amino-5-methylphenol |
| 10.000 g | potassium oleate(8 percent aqueous solution) |
| 10.000 g | ammonia(22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a blond color.

Example 126

HAIR DYE COMPOSITION

A hair dyeing solution having the following composition was prepared:

| | |
|---|---|
| 0.320 g | 2,5-diamino-1-(2-thienyl)benzene*2HCl |
| 0.300 g | 5-amino-2-methylphenol |
| 0.600 g | 4-amino-3-methylphenol |
| 0.600 g | 4-aminophenol |
| 0.100 g | α-naphthol |
| 0.200 g | 2-chloro-6-(ethylamino)-4-nitrophenol |
| 10.000 g | potassium oleate(8 percent aqueous solution) |
| 10.000 g | ammonia (22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a red color.

Example 127

HAIR DYE COMPOSITION

A hair dyeing solution having the following composition was prepared:

| | |
|---|---|
| 0.320 g | 2,5-diamino-1-(2-thienyl)benzene*2HCl |
| 0.040 g | 5-amino-2-methylphenol |
| 0.090 g | 2-amino-4-(2'-hydroxyethyl)amino-anisole sulfate |
| 0.030 g | 3-aminophenol |
| 0.030 g | 1,3-dihydroxybenzene |
| 0.040 g | 1,3-dihydroxy-2-methylbenzene |
| 0.100 g | 4-amino-5-methylphenol |
| 0.200 g | 2-amino-3-methylphenol |
| 0.100 g | 2-amino-6-methylphenol hydrochloride |
| 0.010 g | 4-chloro-N-(2-hydroxyethyl)-2-nitroaniline |
| 0.020 g | 2-amino-4,6-dinitrophenol |
| 0.100 g | 2-chloro-6-(ethylamino)-4-nitrophenol |

| | |
|---|---|
| 10.000 g | potassium oleate(8 percent aqueous solution) |
| 10.000 g | ammonia (22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 128

HAIR DYE COMPOSITION

A hair dyeing solution having the following composition was prepared:

| | |
|---|---|
| 0.320 g | 2,5-diamino-1-(2-thienyl)benzene*2HCl |
| 0.040 g | 5-amino-2-methylphenol |
| 0.050 g | 1,3-diamino-4-(2-hydroxyethoxy)benzene |
| 0.030 g | 3-aminophenol |
| 0.030 g | 1,3-dihydroxybenzene |
| 0.040 g | 1,3-dihydroxy-2-methylbenzene |
| 0.100 g | 4-amino-5-methylphenol |
| 0.200 g | 2-amino-3-methylphenol |
| 0.100 g | 2-amino-6-methylphenol hydrochloride |
| 0.010 g | 4-chloro-N-(2-hydroxyethyl)-2-nitroaniline |
| 0.020 g | 2-amino-4,6-dinitrophenol |
| 0.100 g | 2-chloro-6-(ethylamino)-4-nitrophenol |
| 10.000 g | ammonia(22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 129

HAIR DYE COMPOSITION

A hair dyeing solution having the following composition was prepared:

| | |
|---|---|
| 0.220 g | 2,5-diamino-1-(2-thienyl)benzene*2HCl |
| 0.100 g | 1,4-diamino-2-(2-hydroxyethyl)benzene sulfate |
| 0.020 g | 5-amino-2-methylphenol |
| 0.010 g | 1,3-diamino-4-(2-hydroxyethoxy)benzene sulfate |
| 0.004 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4-amino-3-methylphenol |
| 10.000 g | potassium oleate (8 percent aqueous solution) |
| 10.000 g | ammonia(22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 130

HAIR DYE COMPOSITION

A hair dyeing solution having the following composition was prepared:

| | |
|---|---|
| 0.220 g | 2,5-diamino-1-(2-thienyl)benzene*2HCl |
| 0.100 g | 4-di(2-hydroxyethyl)aminoaniline sulfate |
| 0.020 g | 5-amino-2-methylphenol |
| 0.010 g | 1,3-diamino-4-(2-hydroxyethoxy)benzene |
| 0.015 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4,5-diamino-1-(2-hydoxyethyl)-1H-pyrazole sulfate |
| 10.000 g | potassium oleate(8 percent aqueous solution) |
| 10.000 g | ammonia(22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Example 131

HAIR DYE COMPOSITION

A hair dyeing solution having the following composition was prepared:

| | |
|---|---|
| 0.320 g | 2,5-diamino-1-(2-thienyl)benzene*2HCl |
| 0.020 g | 5-amino-2-methylphenol |
| 0.010 g | 1,3-diamino-4-(2-hydroxyethoxy)benzene |
| 0.015 g | 2-amino-4-(2'-hydroxyethyl)aminoanisole sulfate |
| 0.020 g | 1,3-dihydroxybenzene |
| 0.040 g | 1,3-dihydroxy-2-methylbenzene |
| 0.008 g | 4-amino-2-(aminomethyl)phenol dihydrochloride |
| 10.000 g | potassium oleate(8 percent aqueous solution) |
| 10.000 g | ammonia(22 percent aqueous solution) |
| 10.000 g | isopropanol |
| 0.300 g | ascorbic acid |
| | ad water to 100 g |

30 g of the above-described dye solution were mixed immediately prior to use with 30 g of a 6 percent by weight hydrogen peroxide solution. Subsequently the mixture was applied to bleached hair. After an acting time of 30 minutes at 40° C. the hair is rinsed with water, washed with a commercial shampoo and dried. The hair dyed in this way had a brown color.

Unless otherwise indicated all percentages are percentages by weight.

While the invention has been illustrated and described as embodied in new diaminobenzene derivative compounds and dye compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

We Claim:

1. A dye composition for oxidative dyeing of keratin fibers, said dye composition containing a combination of coupler and developer substances, said developer substance comprising at least one p-diaminobenzene derivative compound of the formula (I):

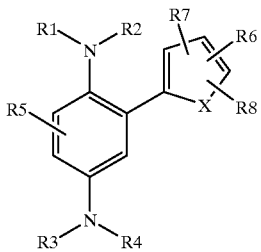

(I)

wherein X represents oxygen, sulfur, selenium or N—R9;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four-membered to eight-membered aliphatic ring, with the proviso that at least 2 of the R1 to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

is R6 and R8 each, independently of each other, represents hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxy-alkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 represents hydrogen, a halogen atom, a $C_1$- to $C_6$-alkyl group or a —C(O)H group;

R9 represents hydrogen, a $C_1$- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11, R13 and R16 each, independently of each other, represents hydrogen or a $C_1$- to $C_4$-alkyl group;

R12 represents an amino group or a nitrile group; R14, R17 and R18 each, independently of each other, represents hydrogen, a hydroxy group, a $C_1$- to $C_4$-alkyl group, a $C_1$- to $C_4$-hydroxyalkyl group, a $C_3$- to $C_4$-dihydroxyalkyl group or a group of formula (II):

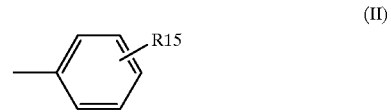

(II)

and R15 represents hydrogen, an amino group or a hydroxy group;

or a physiologically compatible salt thereof.

2. The composition as defined in claim 1, wherein one or more of said R5, R6, R7 and R8 represent said hydrogen.

3. The composition as defined in claim 1, wherein each of said R1, R2, R3 and R4 represents said hydrogen.

4. The composition as defined in claim 1, wherein said R7 represents said hydrogen and said R6 group represents said hydrogen, said —C(O)H group, said —C(O)CH$_3$ group, a $C_1$- to $C_4$-alkyl group or said $C_1$- to $C_4$-hydroxyalkyl group.

5. The composition as defined in claim 4, wherein each of said R7 and R6 represents said hydrogen.

6. The composition as defined in claim 1, wherein said at least one p-diaminobenzene derivative compound is selected from the group consisting of 2,5-diamino-1-(2-thienyl) benzene, 2,5-diamino-1-(2-furyl)benzene, 2,5-diamino-1-(3-acetyl-2-thienyl)benzene, 2,5-diamino-1-(3-chloro-2-thienyl)benzene, 2,5-diamino-1-(1H-pyrrol-2-yl)benzene, 2,5-diamino-1-(3-methyl-2-thienyl)-benzene, 2,5-diamino-1-(5-methyl-2-thienyl)-benzene, 2,5-diamino-1-(3-nitro-2-thienyl)benzene, 2-dimethylamino-5-amino-1-(2-thienyl) benzene, 2-pyrrolidino-5-amino-1-(2-thienyl)benzene, 2-di (2-hydroxyethyl)amino-5-amino-1-(2-thienyl)benzene, 2-(2-hydroxyethyl)amino-5-amino-1-(2-thienyl)benzene, 2-(2-methoxyethyl)amino-5-amino-1-(2-thienyl)benzene, 2-(2,3-dihydroxypropyl)amino-5-amino-1-(2-thienyl) benzene, 2,5-diamino-4-methoxy-1-(2-thienyl)benzene, 2,5-diamino-4-methyl-1-(2-thienyl)-benzene, 2,5-diamino-1-(3-chloro-2-thienyl)benzene, 2,5-diamino-1-(1-methylpyrrol-2-yl)benzene and 2,5-diamino-1-(3-formyl-2-thienyl) benzene.

7. The composition as defined in claim 1 containing from 0.005 to 20.0 percent by weight of said at least one p-diaminobenzene derivative compound or said salt.

8. The composition as defined in claim 1, wherein said coupler substance is selected from the group consisting of 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methyl-benzene, 2,4-diamino-1-(2-hydroxyethoxy)-5-methylbenzene, 2,4-di[(2-hydroxyethyl) amino]-1,5-dimethoxy-benzene, 2,3-diamino-6-methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di-(2-hydroxy-ethoxy)benzene, 1-(2-aminoethoxy)-2,4-diaminobenzene, 2-amino-1-(2-hydroxyethoxy)-4-methylaminobenzene, 2,4-diaminophenoxy-acetic acid, 3-[di-(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)-methane, 1,3-diamino-2,4-dimethoxy-benzene, 2,6-bis-(2-hydroxyethyl)aminotoluene, 4-hydroxyindole, 3-dimethylamino-phenol, 3-diethylaminophenol, 5-amino-2-methylphenol, 5-amino-4-fluoro-2-methylphenol, 5-amino-4-methoxy-2-methyl-phenol, 5-amino-4-ethoxy-2-methyl-phenol, 3-amino-2,4-dichlorophenol, 5-amino-2,4-dichlorophenol,3-amino-2-methyl-phenol, 3-amino-2-chloro-6-methylphenol, 3-amino-phenol, 2-[(3-hydroxyphenyl)amino]acetamide, 5-[(2-hydroxy-ethyl)-amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)-amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxy-benzene, 1-chloro-2,4-dihydroxybenzene, 2-chloro-1,3-dihydroxybenzene, 1,2-dichlor- 3,5-dihydroxy-4-methyl-benzene, 1,5-dichloro-2,4-dihydroxybenzene, 1,3-dihydroxy-2-methylbenzene, 3,4-methylendioxyphenol, 3,4-methylendioxy-aniline, 5-[(2-hydroxyethyl)amino]-1,3-benzodioxole, 6-bromo-1-hydroxy-3,4-methylendioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindolene, 5-hydroxyindole, 6-hydroxyindole, 7-hydroxyindole and 2,3-indolindione.

9. The composition as defined in claim 1, wherein said developer substance contains at least one member selected from the group consisting of 1,4-diaminobenzene, 2,5-diamino-toluene, 2,5-diaminophenylethyl alcohol, 4-aminophenol, substituted 4-aminophenols, substituted 4,5-diaminopyrazoles and tetraaminopyrimidines.

10. The composition as defined in claim 1, containing a total amount of 0.005 to 20 percent by weight of said developer substance and said coupler substance.

11. The composition as defined in claim 1, further comprising at least one direct-dyeing dye compound.

12. The composition as defined in claim 11, wherein said at least one direct-dyeing dye compound is selected from the group consisting of triphenylmethylene dye compounds, aromatic nitro dye compounds, azo dye compounds and dispersion dye compounds.

13. The composition as defined in claim 1, having a pH of from 6.8 to 11.5.

14. The composition as defined in claim 1, in the form of an aqueous or aqueous-alcoholic solution, a cream, a gel or an emulsion.

15. The composition as defined in claim 1, further comprising at least one cosmetic additive ingredient appropriate for hair dyeing compositions.

16. The composition as defined in claim 15, wherein said at least one cosmetic additive ingredient is selected from the group consisting of solvents, wetting agents, emulsifiers, thickeners, hair care materials, antioxidants, perfumes and complexing agents.

17. A p-diaminobenzene derivative compound of the formula (I):

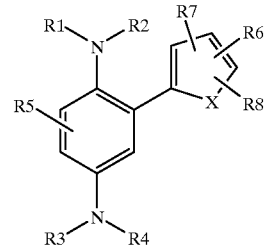

(I)

wherein X represents oxygen, sulfur, selenium or N-R9;

R1, R2, R3 and R4 each, independently of each other, represents hydrogen, a $C_1$- to $C_6$-alkyl group, a $C_1$- to $C_4$-hydroxyalkyl group, a $C_2$- to $C_4$-dihydroxyalkyl group or a $C_1$- to $C_4$-alkoxy-($C_1$- to $C_2$)-alkyl group or R1 and R2 or R3 and R4 represent a four membered to eight membered aliphatic ring, with the proviso that at least 2 of the R1 to R4 groups represent hydrogen;

R5 represents hydrogen, a halogen atom, a $C_1$- to $C_4$-alkyl group, a $C_1$- to $C_4$-hydroxyalkyl group or a $C_1$- to $C_4$-alkoxy group;

R6 and R8 each, independently of each other, represents hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, an alkylamino group, a dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR10 group, a —(CH$_2$)$_p$—CO$_2$R11 group or a —(CH$_2$)$_p$R12 group with p=1, 2, 3 or 4, a —C(R13)=NR14 group or a —C(R16)H—NR17R18 group;

R7 represents hydrogen, a halogen atom, a $C_1$- to $C_6$-alkyl group or a —C(O)H group;

R9 represents hydrogen, a $C_1$- to $C_6$-alkyl group, a $C_1$- to $C_4$-hydroxyalkyl group, a phenyl group or an acetyl group;

R10 represents hydrogen, a hydroxy group, a nitro group, an amino group, a —CO$_2$R11 or a —C(O)CH$_3$ group;

R11 , R13 and R16 each, independently of each other, represents hydrogen or a $C_1$- to $C_4$-alkyl group;

R12 represents an amino group or a nitrile group;

R14, R17 and R18 each, independently of each other, represent hydrogen, a hydroxy group, a $C_1$- to $C_4$-alkyl group a $C_1$- to $C_4$-hydroxyalkyl group, a $C_3$- to $C_4$-dihydroxyalkyl group or a group of formula (II):

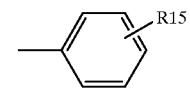

(II)

and R15 represents hydrogen, an amino group or a hydroxy group;

with the proviso that, if X represents oxygen and both R1 and R2 represent a methyl group, at least one of the groups R3 to R8 is not hydrogen;

or a physiologically compatible salt thereof.

18. The p-diaminobenzene derivative compound as defined in claim 17, wherein at least one of said R1, R2, R3, R4, R5, R6, R7 and R8 represents said hydrogen and/or said R1, R2, R3 and R4 each represents said hydrogen and/or said R7 represents said hydrogen and said R6 represents said hydrogen, —C(O)H, —C(O)CH$_3$, C$_1$–C$_4$-alkyl group or C$_1$–C$_4$-hydroxyalkyl group.

19. The p-diaminobenzene derivative compound as defined in claim 17, wherein said at least one p-diaminobenzene derivative compound is selected from the group consisting of 2,5-diamino-1-(2-thienyl)benzene, 2,5-diamino-1-(2-furyl)benzene, 2,5-diamino-1-(3-acetyl-2-thienyl)benzene, 2,5-diamino-1-(3-chloro-2-thienyl)benzene, 2,5-diamino-1-(1H-pyrrol-2-yl)benzene, 2,5-diamino-1-(3-methyl-2-thienyl)-benzene, 2,5-diamino-1-(5-methyl-2-thienyl)-benzene, 2,5-diamino-1-(3-nitro-2-thienyl)benzene, 2-dimethylamino-5-amino-1-(2-thienyl) benzene, 2-pyrrolidino-5-amino-1-(2-thienyl)benzene, 2-di (2-hydroxyethyl)amino-5-amino-1-(2-thienyl)benzene, 2-(2-hydroxyethyl)amino-5-amino-1-(2-thienyl)benzene, 2-(2-methoxyethyl)amino-5-amino-1-(2-thienyl)benzene, 2-(2,3-dihydroxypropyl)amino-5-amino-1-(2-thienyl) benzene, 2,5-diamino-4-methoxy-1-(2-thienyl)benzene, 2,5-diamino-4-methyl-1-(2-thienyl)-benzene, 2,5-diamino-1-(3-chloro-2-thienyl)benzene, 2,5-diamino-1-(1-methylpyrrol-2-yl)benzene and 2,5-diamino-1-(3-formyl-2-thienyl) benzene.

\* \* \* \* \*